(12) United States Patent
Schwartz

(10) Patent No.: US 9,125,722 B2
(45) Date of Patent: Sep. 8, 2015

(54) DEVICE FOR THE ULTRASONIC TREATMENT OF GLAUCOMA HAVING A CONCAVE TIP

(71) Applicant: Donald N. Schwartz, Long Beach, CA (US)

(72) Inventor: Donald N. Schwartz, Long Beach, CA (US)

(*) Notice: Subject to any disclaimer, the term of this patent is extended or adjusted under 35 U.S.C. 154(b) by 243 days.

(21) Appl. No.: 13/762,272

(22) Filed: Feb. 7, 2013

(65) Prior Publication Data

US 2013/0211395 A1 Aug. 15, 2013

Related U.S. Application Data

(60) Provisional application No. 61/597,102, filed on Feb. 9, 2012.

(51) Int. Cl.
*A61H 1/00* (2006.01)
*A61F 9/00* (2006.01)
*A61F 9/007* (2006.01)
*A61B 17/00* (2006.01)
*A61B 17/32* (2006.01)

(52) U.S. Cl.
CPC ......... *A61F 9/00781* (2013.01); *A61F 9/00745* (2013.01); *A61B 2017/00738* (2013.01); *A61B 2017/320072* (2013.01)

(58) Field of Classification Search
None
See application file for complete search history.

(56) References Cited

U.S. PATENT DOCUMENTS

| 4,484,569 | A  | * | 11/1984 | Driller et al. ............... 600/439 |
|-----------|----|---|---------|----------------------------------------|
| 5,779,696 | A  |   | 7/1998  | Berry et al.                           |
| 6,051,010 | A  | * | 4/2000  | DiMatteo et al. ............. 606/169  |
| 6,162,193 | A  | * | 12/2000 | Ekberg ........................... 604/22 |
| 2001/0014780 | A1 |   | 8/2001  | Martin et al.                        |
| 2008/0051681 | A1 | * | 2/2008  | Schwartz ........................ 601/2 |
| 2008/0177220 | A1 |   | 7/2008  | Lindgren et al.                      |
| 2010/0152626 | A1 |   | 6/2010  | Schwartz                             |
| 2011/0009779 | A1 | * | 1/2011  | Romano et al. .................. 601/2 |
| 2012/0116221 | A1 | * | 5/2012  | Sehgal et al. ................. 600/439 |

OTHER PUBLICATIONS

International Search Report and Written Opinion issued on May 13, 2013 in PCT/US 13/25440.

* cited by examiner

*Primary Examiner* — Long V Le
*Assistant Examiner* — Bradley Impink
(74) *Attorney, Agent, or Firm* — Jeffer Mangels Butler & Mitchell LLP; Brennan C. Swain, Esq.

(57) ABSTRACT

A handheld device for the treatment of glaucoma that includes a casing, an ultrasonic transducer, a power supply, a transmission member operatively associated with the ultrasonic transducer, and a tip member located at the end of the transmission member. The ultrasonic energy is transferred from the ultrasonic transducer to the tip member. The tip includes a concave eye-engaging surface.

11 Claims, 9 Drawing Sheets

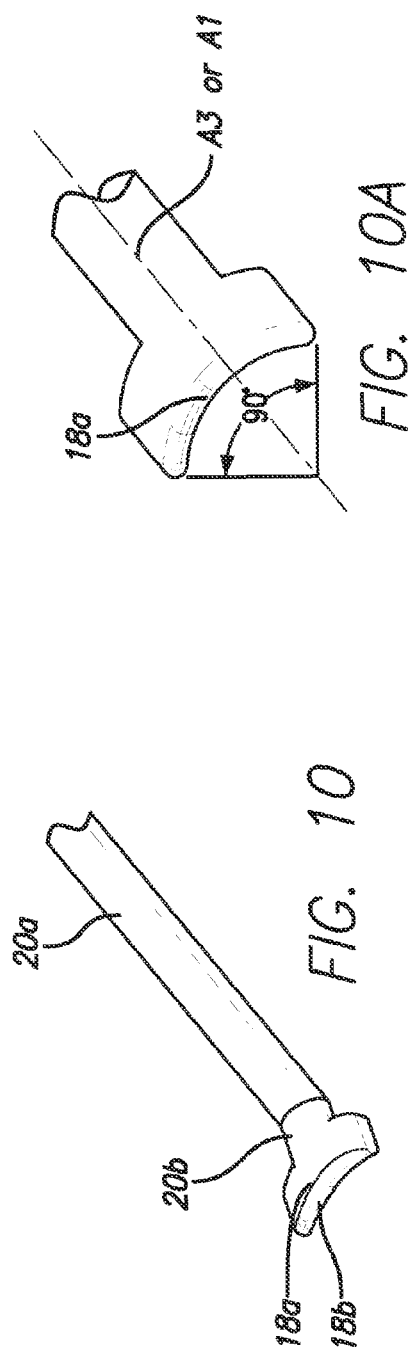
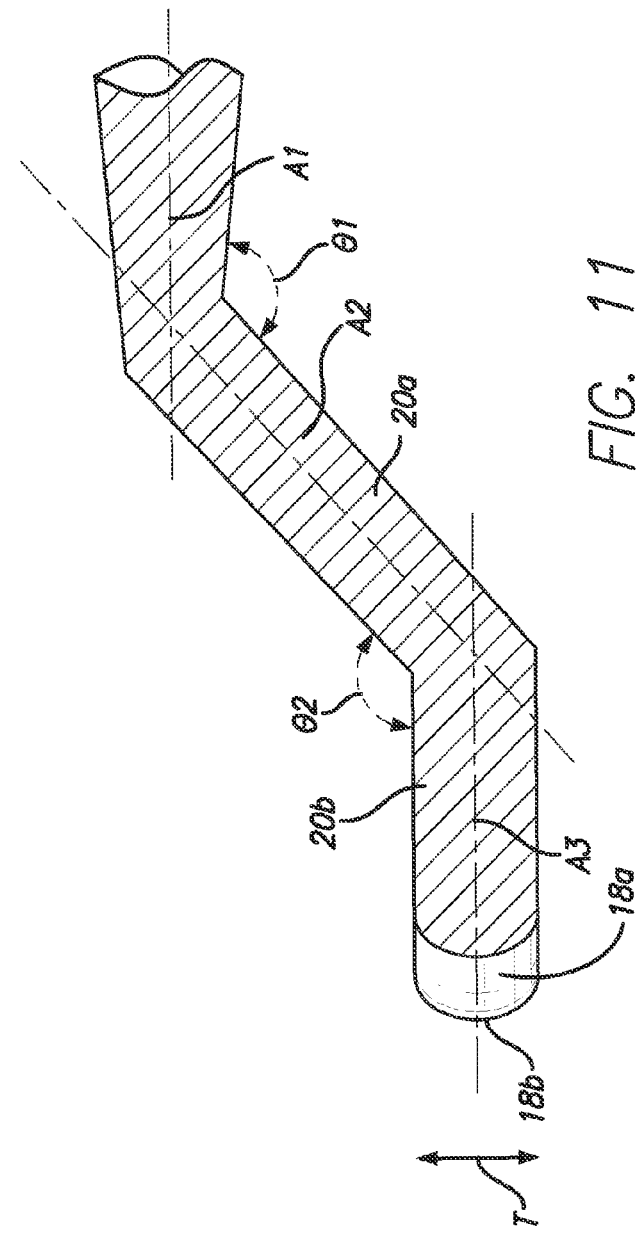

DEVICE FOR THE ULTRASONIC TREATMENT OF GLAUCOMA HAVING A CONCAVE TIP

This application claims the benefit of U.S. Provisional Application No. 61/597,102, filed Feb. 9, 2012, which is herein incorporated by reference in its entirety.

FIELD OF THE INVENTION

The present invention relates generally to a device for the treatment of glaucoma and, more particularly, to a device for the treatment of glaucoma that has a curved tip.

BACKGROUND OF THE INVENTION

Open angle glaucoma exists when the pressure in the eye is not tolerated by the patient and is causing damage to the optic nerve. The current treatment for open angle glaucoma is aimed at reducing the intraocular pressure to a level that is safe for the patient's eye, to preserve vision.

Open angle glaucoma is treated with pharmaceutical agents. Another method of treatment, laser treatment for open angle glaucoma, has been reserved for medical treatment failures but is gaining some favor as a primary treatment. Another approach, intraocular surgery, is reserved for medical and/or laser failures.

Frequently, the increased pressure in the eye is caused by a blockage in the ability of the fluid to leave the eye, not an actual increase of the fluid itself. As shown in FIG. 1, the blockage is typically in the part of the trabecular meshwork near Schlemm's canal, called the juxtacanalicular meshwork. The meshwork is typically blocked, by anatomical changes, pigment, extracellular matrix debris or pseudoexfoliative material.

Medical treatment is directed at decreasing the production of the fluid (aqueous humor) or enhancing the ability of the fluid to leave the eye. Medical treatment is not curative. It is used on a continuing basis to decrease the pressure. But, when the treatment is stopped the pressure rises. Also, medical treatment demands patient compliance, has unwanted side effects, is expensive, and may interact poorly with other medical care for the patient.

Laser treatment has been partially successful in its original (argon) method. Newer laser treatment, such as selective laser trabeculoplasty, is gaining favor. However, laser treatment is performed on the inside of the eye and treats the inner, not the outer, trabecular meshwork. With this treatment, there is a secondary physiologic response that leads to an increase in fluid outflow after the laser is performed.

Frequently, after modern day cataract surgery there is a decrease in the intraocular pressure as an unintended positive side effect. Typical modern cataract surgery removes the cataract by ultrasonic eraulsification of the lens material. This method is known as phacoemulsification. Older cataract surgery, without implants, removed more material from inside the eye, but the decrease in intraocular pressure was not as consistent as with modern day or current surgery. It is believed that the ultrasound used to break up the lens material helps dislodge the built up material. However, this is just a side effect, and, as described below, the ultrasonic energy used in phacoemulsification is intense enough to damage tissue.

Accordingly, a need exists for a treatment of glaucoma that includes a method of applying ultrasonic energy to the eye to dislodge built up material and initiate biochemical processes to reduce and remove extracellular debris, thereby decrease pressure, and that can be performed without damaging tissue. See U.S. Pat. Nos. 7,909,781 and 8,043,235 to Schwartz, the entireties of which are incorporated, herein by reference.

SUMMARY OF THE PREFERRED EMBODIMENTS

In accordance with a first aspect of the present invention there is provided a handheld device for the treatment of glaucoma that includes a casing, an ultrasonic transducer, a power supply, a transmission member operatively associated with the ultrasonic transducer, and a tip member located at the end of the transmission member. The ultrasonic energy is transferred from the ultrasonic transducer to the tip member. The tip includes a concave eye-engaging surface. In a preferred embodiment, the concave eye-engaging surface defines an arc that is between about 45° and about 180°. In a preferred embodiment, the concave eye-engaging surface defines an arc that is about 90° with an arc length of between about 6.5 mm and about 11.5 mm. The tip member defines a thickness direction, and preferably the concave eye-engaging surface includes a convex shape in the thickness direction. In a preferred embodiment, the transmission member includes a first angled extension member disposed between the ultrasonic transducer and the tip member. The transmission member defines a first axis and the first angled extension member defines a second axis, and the first axis and second axis are not parallel to one another. In a preferred embodiment, the transmission member includes a second angled extension member disposed between the first angled extension member and the tip member. The second angled extension member defines a third axis, and the first axis and the third axis are about parallel to one another. In another embodiment, the first axis and the third axis are not parallel to one another. In an embodiment without the first and second angled extension members, the first axis extends through a center of a circle defined by the arc. In an embodiment with the first and second angled extension members, the third axis extends through a center of a circle defined by the arc.

In accordance with another aspect of the present invention there is provided a method of treating glaucoma that includes the steps of selecting a device that emits ultrasonic energy and that includes a tip member having a concave eye-engaging surface that defines an arc between about 45° and about 180°, holding the device at a location external to the trabecular meshwork and adjacent a first arc of the circumference of the limbus and transmitting ultrasonic energy at a frequency to a desired location for a predetermined time, and holding the device at a location external to the trabecular meshwork and adjacent a second arc of the circumference of the limbus and transmitting ultrasonic energy at a frequency to a desired location for a predetermined time. In a preferred embodiment, the concave eye-engaging surface defines an arc that is about 90° and the method includes the steps of holding the device at a location external to the trabecular meshwork and adjacent a third arc of the circumference of the limbus and transmitting ultrasonic energy at a frequency to a desired location for a predetermined time, and holding the device at a location external to the trabecular meshwork and adjacent a fourth arc of the circumference of the limbus and transmitting ultrasonic energy at a frequency to a desired location for a predetermined time. The method preferably also includes the step of increasing the temperature of a portion of the eye to a temperature of between about 41 and about 45 degrees centigrade to initiate a biochemical cascade within the eye, wherein the biochemicals reduce and remove extracellular debris from the trabecular meshwork.

In a preferred embodiment, the ultrasonic energy is focused at a point between about 0.5 mm and about 2.0 mm from the concave eye-engaging surface, the frequency is between about 20,000 Hertz and about 100,000 Hertz and the time is between about 5 seconds and about 120 seconds. In performing the method, there is preferably a release of cytokines that causes a reduction in intraocular pressure in the eye. The release of cytokines may cause a reduction in intraocular pressure in the subject's other eye. Furthermore, the method preferably initiates heat shock proteins, stimulates matrix metalloprotemase and/or induces macrophage activity and can include increasing the temperature of a portion of the eye to cause an inflammatory reaction that initiates the biochemical cascade within the eye. Preferably, the focused ultrasound does not cause tissue damage within the eye.

In use, the device is held at a location external to the trabecular meshwork of a subject's eye, the device transmits focused ultrasonic energy at a frequency between about 20,000 Hertz and about 100,000 Hertz to a desired location in the eye for a predetermined time, and wherein the temperature of a portion of the eye is increased such that a biochemical cascade is initiated within the eye, and the biochemicals reduce and remove extracellular debris from the trabecular meshwork.

In accordance with an embodiment of the invention, there is provided an ultrasonic device that includes a tip with a concave shape for treating eyes with glaucoma. The transmission member of the device includes first and second angled extension members and the tip includes a concave portion that extends in a width direction and a convex portion that extends in a thickness direction. In a preferred embodiment, the arc of the concave portion at the treatment end is about 90°.

In accordance with another aspect of the present invention, there is provided a method of treating glaucoma. The method includes the steps of providing an ultrasonic device that emits ultrasonic energy, holding the ultrasonic device at a location external to the trabecular meshwork, transmitting the ultrasonic energy at a frequency to a desired location for a predetermined time, causing biochemical changes to be initiated within the eye that may include triggering a presumed integrin response that initiates biochemical changes typified by but not limited to cytokines, enzymes, macrophage activity and heat shock proteins, and dislodging material built up in the trabecular meshwork. In a preferred embodiment, the tip includes a curved portion.

In accordance with another aspect of the present invention, there is provided, a handheld, ultrasonic device that includes a casing, an ultrasonic transducer disposed in the casing, a power supply, a transmission member extending from the ultrasonic transducer, and a tip located at the end of the transmission member. Ultrasonic energy is transferred from the ultrasonic transducer to the tip. In a preferred embodiment, the casing is attached to the ultrasonic transducer at a null point.

The device disclosed herein preferably includes a metallic tip and focused ultrasound that is aimed at increasing/triggering integrals, and elevating the temperature within the treatment area to a level that begins a biochemical cytokine cascade that is then absorbed systemically leading to a decrease in intraocular pressure in both eyes.

The invention, together with additional features and advantages thereof, may be best understood by reference to the following description.

BRIEF DESCRIPTION OF THE DRAWINGS

The invention may be more readily understood by referring to the accompanying drawings in which:

FIG. 8A is a perspective view of an ultrasonic device used for treatment of glaucoma in accordance with another preferred embodiment of the present invention;

FIG. 10 is a detailed perspective view of the tip of the device of FIG. 8;

FIG. 10A demonstrates that, in a preferred embodiment, the concave tip of the device of FIG. 8 forms an arc of about 90 degrees;

FIG. 11 is a cross-sectional view taken along line 11-11 of FIG. 8; and

Like numerals refer to like parts throughout the several views of the drawings.

DETAILED DESCRIPTION OF THE PREFERRED EMBODIMENTS

Figure 1:
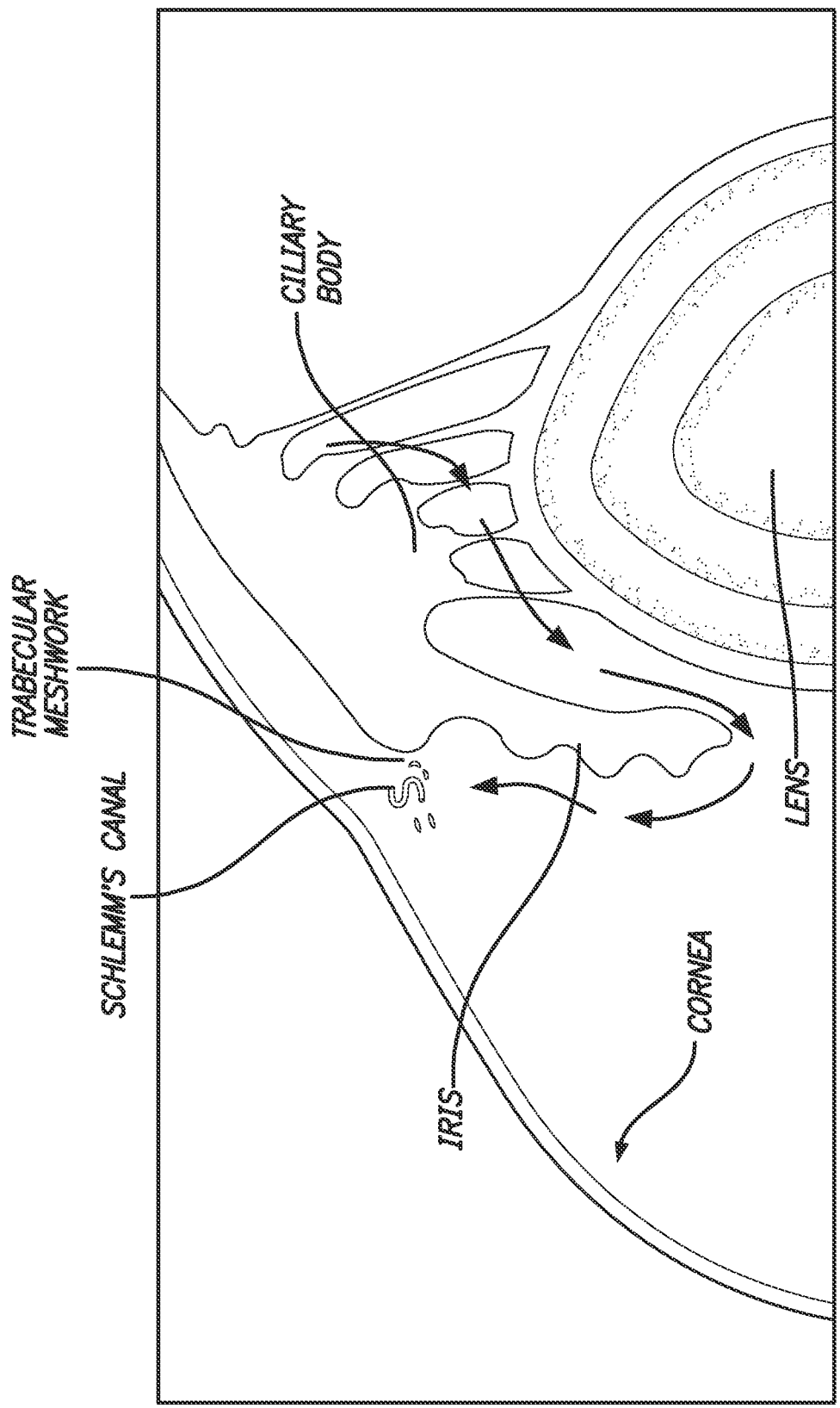
FIG. 1 is a view of a portion of the inside of an eye.

The following description and drawings are illustrative and are not to be construed as limiting. Numerous specific details are described to provide a thorough understanding of the disclosure. However, in certain instances, well-known or conventional details are not described in order to avoid obscuring the description. References to one or an other embodiment in the present disclosure can be, but not necessarily are, references to the same embodiment; and, such references mean at least one of the embodiments.

Reference in this specification to "one embodiment" or "an embodiment" means that a particular feature, structure, or characteristic described in connection with the embodiment is included in at least one embodiment of the disclosure. Appearances of the phrase "in one embodiment" in various places in the specification do not necessarily refer to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks: The use of highlighting has no influence on the scope and meaning of a term; the scope and meaning of a term is the same, in the same context, whether or not it is highlighted. It will be appreciated that the same thing can be said in more than one way.

Consequently, alternative language and synonyms may be used for any one or more of the terms discussed herein. Nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any exemplified term. Likewise, the disclosure is not limited to various embodiments given in this specification.

Without intent to further limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions, will control.

It will be appreciated that terms such as "front," "back," "top," "bottom," "side," "short," "long," "up," "down," and "below" used herein are merely for ease of description and refer to the orientation of the components as shown in the figures. It should be understood that any orientation of the components described herein is within the scope of the present invention.

Referring now to the drawings, wherein the showings are for purposes of illustrating the present invention and not for purposes of limiting the same, FIGS. 1-11 show instruments used for treating glaucoma.

Described herein are preferred embodiments of a method for the ultrasonic treatment of glaucoma. The method includes the use of tools that are shown in FIGS. 3-11.

Generally, the method includes providing ultrasonic energy to induce cytokines in a desired area of the eye to dislodge and/or remove material from the trabecular meshwork, thereby lowering the pressure within the eye. The presently described methods are used to reduce the pressure build up in the eye described above.

Figure 2:
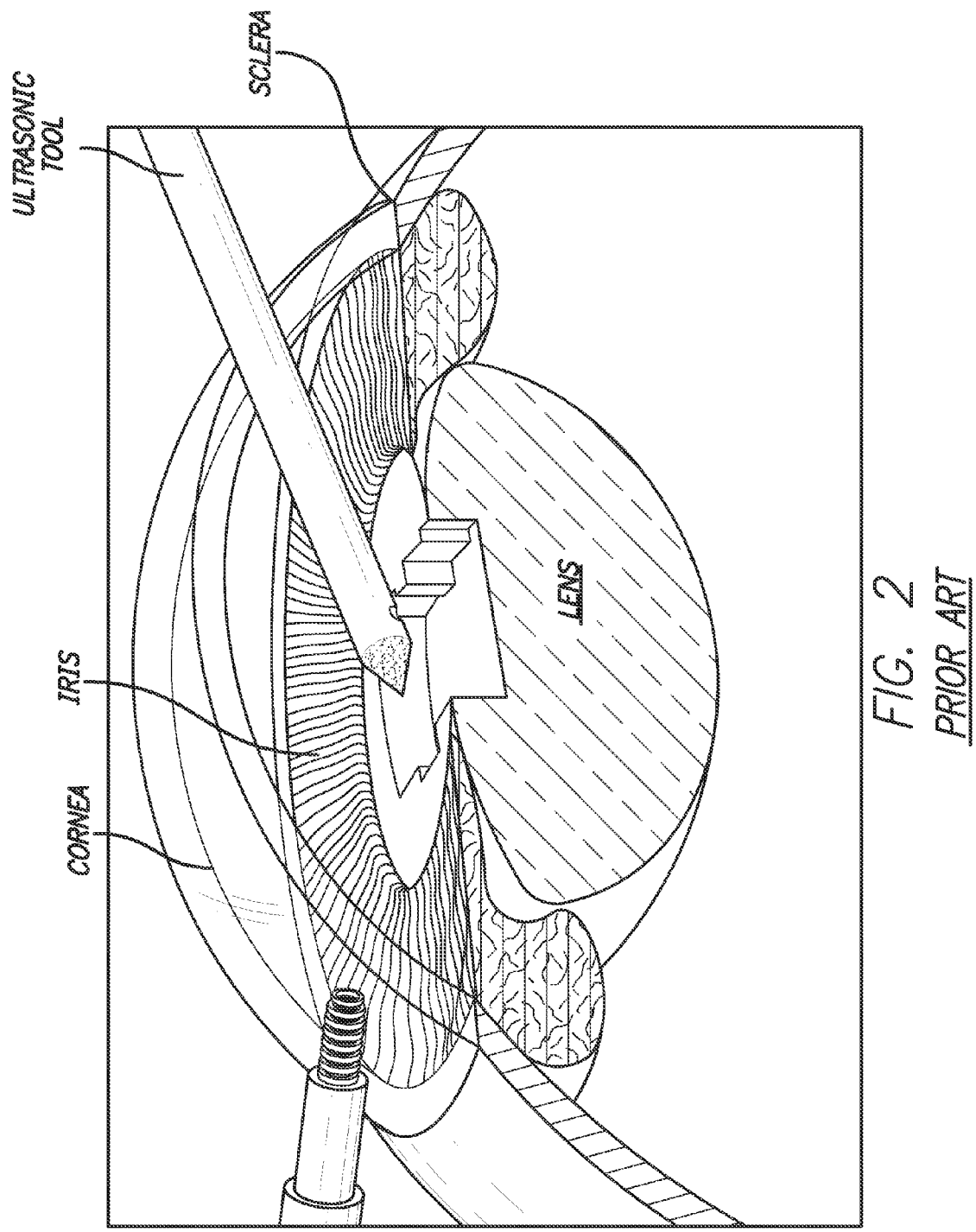
FIG. 2 is a view of a portion of the inside of an eye that includes instruments used in phacoemulsification.

FIG. 2 shows phacoemulsification being performed on an eye. As is described, the technique of phacoemulsification has been shown to cause a decrease of pressure in the eye. However, the ultrasound intensity used in phacoemulsification is quite vigorous and is designed to carve the lens tissue or disrupt its anatomy. As can be seen in FIG. 2, the instrument is actually in contact with the lens. In addition, the commonly used ultrasound instrument for phacoemulsification has a tip that is pointed and sharp, is designed to engage the tissue in the eye directly and has three inputs for ultrasound, irrigation and aspiration.

In a preferred embodiment of the present invention, the instruments (described below) focus the energy of the ultrasound a distance from the tissue and do not engage it directly. Moreover, the ultrasound intensity is preferably significantly less vigorous than phacoemulsification and, therefore, creates acoustic energy at a much gentler intensity. Lastly, the specific area and focus of the treatment is the anterior chamber angle including the ciliary body and trabecular meshwork in the anterior portion of the globe, and not the crystalline lens of the eye, as in phacoemulsification.

The forces obtained from ultrasound treatment are complex, but an fit into three categories: sonomechanical, heat generated and integrin triggering. For example, see U.S. Patent Pub. No. 2006/0106424 to Bachem and U.S. Pat. No. 6,162,193 to Ekberg, the entireties of which are incorporated herein by reference. Ultrasound creates microbubbles which may implode vigorously and thereby create heat and violent micromovement. This is known as cavitation. This creation of microbubbles and subsequent implosion with heat is either stable or unstable (transient). The stable cavitation is less likely to lead to cell necrosis and tissue damage. In addition there is an effect of the wavefront of the ultrasound that creates a phenomenon of streaming that allows the movement of particles within a fluid.

The device 10 for the treatment of glaucoma by ultrasound described below in chides a balance such that the frequency, power and duration of the propagated ultrasound has the optimum balance of controlled cavitation, heat and acoustic streaming to effect the trabecular meshwork. The effect is such that debris, or other occlusive structures, may be dislodged to create a larger outflow by the forces mentioned above. In addition the nature of the heat generated and the subsequent inflammatory reaction and integrin absorption of ultrasound with the release of cytokines is directed to initiating cascades of biochemical reactions that lead to remodeling of the extracellular matrix and induction of macrophages to remove extracellular debris to further enhance the long term effect of the treatment. It will be understood that performance of the method described herein causes an inflammatory response that causes the cells to release cytokines. The cytokines trigger enzymes and macrophage activity. The enzymes break down the extracellular debris clogging the trabecular meshwork and the macrpophages clear the broken down debris.

Described herein are instruments used for ultrasonically treating the eye for use on the surface of the eye (external), which can be used without having to enter the interior of the eye.

Figure 3:
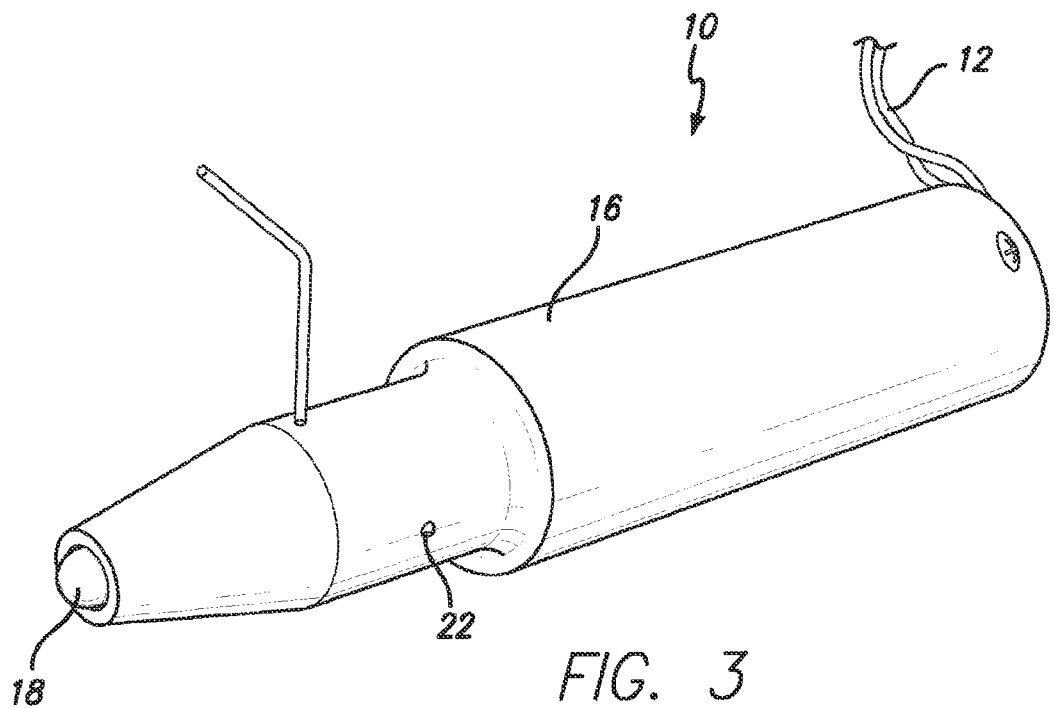
FIG. 3 is a perspective view of an ultrasonic device used for treatment of glaucoma that is used external of the eye, in accordance with a preferred embodiment of the present invention.
Figure 4:
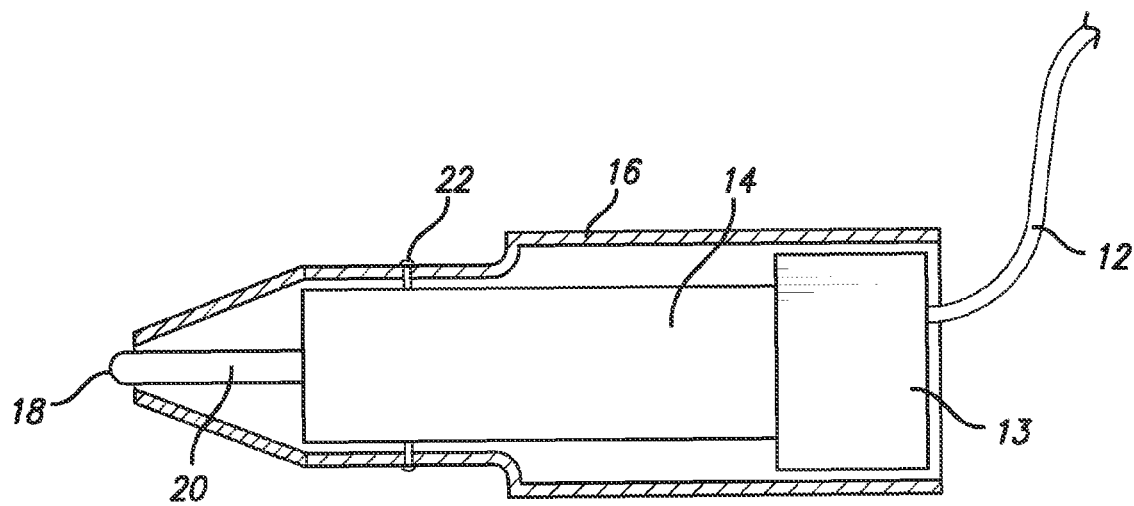
FIG. 4 is a cross-sectional side elevational view of the device of FIG. 3.
Figure 5:
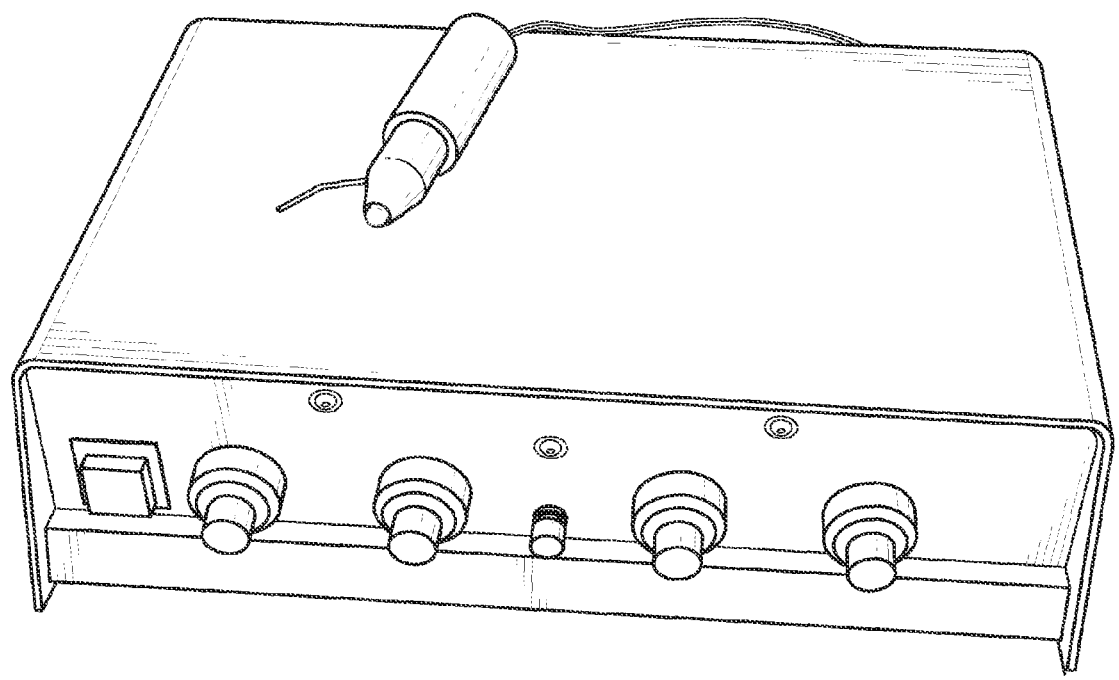
FIG. 5 a perspective view of the ultrasonic device of FIG. 3 along with a power supply.
Figure 6:
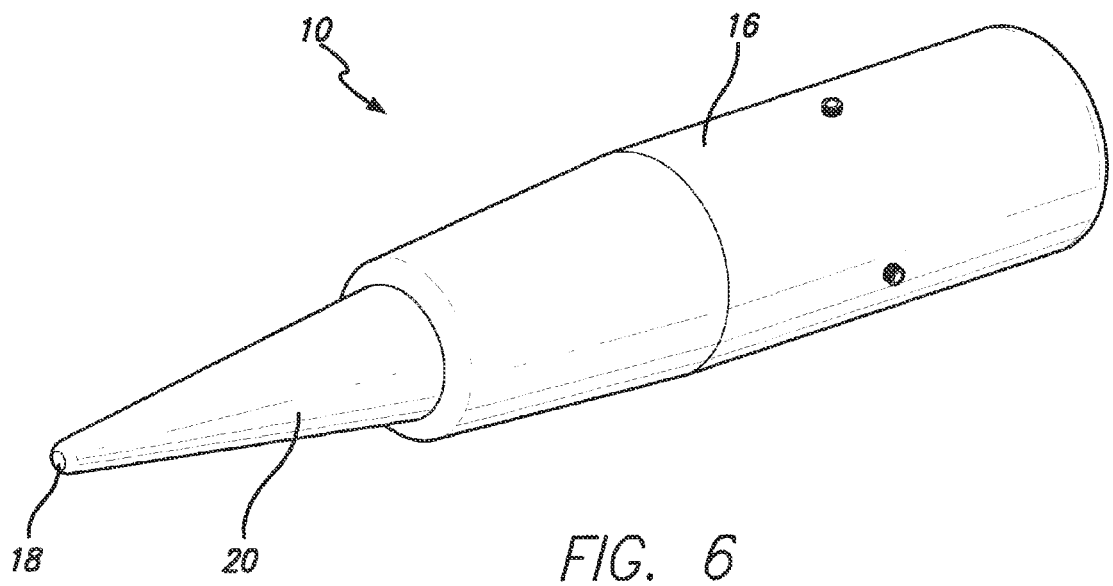
FIG. 6 is a perspective view of an ultrasonic device used for treatment of glaucoma that is used external of the eye, in accordance with another preferred embodiment of the present invention.
Figure 7:
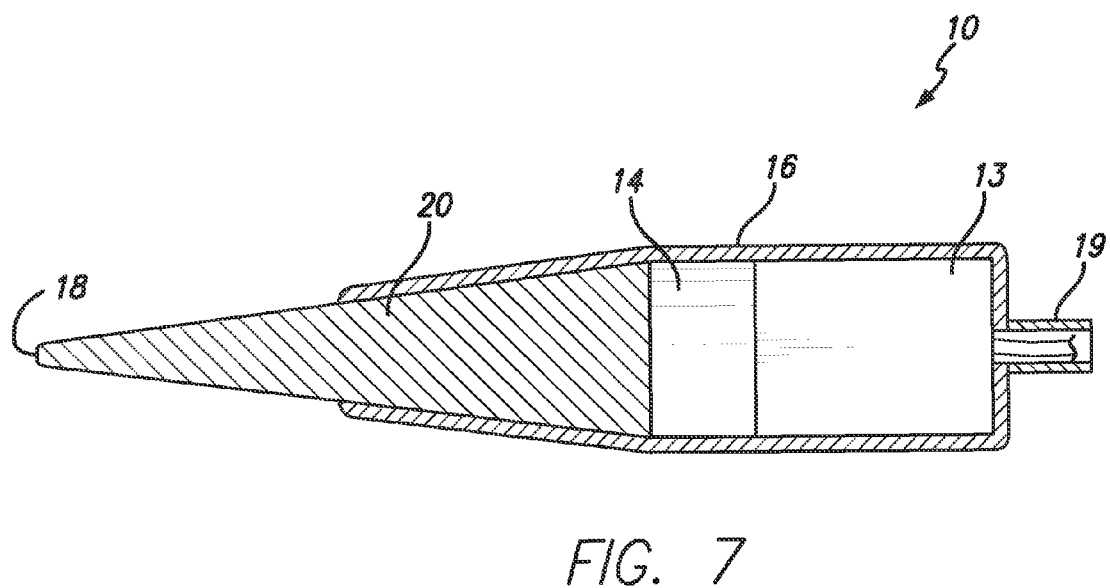
FIG. 7 is a cross-sectional side elevational view of the device of FIG. 6.

Referring to FIGS. 3-5, a device or probe 10 for treatment on the outside surface of the eye is shown. Generally, the device 10 includes a power cord 12, a power supply 13 and an ultrasonic transducer 14 housed within a casing 16. It is contemplated that either AC or DC power can be used. However, in a preferred embodiment, DC power is provided (which may be from alternating current and then converted to DC or it may be from a battery pack). It will be understood by those skilled in the art that the type of ultrasonic transducer is not a limitation on the present invention. For example, the ultrasonic energy can be provided by piezoelectrics, liquids, crystals, etc. See, for example, U.S. Pat. No. 6,616,030 to Miller, which is incorporated by reference in its entirety herein. In the example shown in the figures, the ultrasonic transducer 14 uses piezoelectric technology. The ultrasonic energy produced by the transducer 14 is transmitted down a transmission member or rod 20 and to the tip 18. Preferably, the tip 18 is smooth and rounded with a surface that allows for appropriate gel or liquid interface to the ocular surface. The smooth tip is preferred over the sharp tip of the prior art to prevent laceration of the exterior ocular surface or the cornea. In another embodiment, as shown in FIGS. 6-7, the tip 18 is round or circular, but generally flat.

In a preferred embodiment, the casing 16 is attached to the transducer at a null point so as to not upset, or diminish ultrasound production within the casing; but avoiding contact with the tip to 18 allow maximum energy. As shown in FIG.

4, there is a space between the casing 16 and rod 20 and/or tip 18. The casing 16 can be attached to the transducer, for example, by threaded fasteners 22, rivets or the like.

As shown in FIGS. 3-5, the casing 16 has is shaped so that it fits easily into a user's hand. In a preferred embodiment, the casing 16 includes a handle 24 extending therefrom that can be grasped by a user's second hand. With this design the user can grasp the casing 16 with one hand and use the other hand to guide the device 10 using the handle 24. This provides a greater ability to manipulate the device 10 as desired. The handle 24 may be straight or bent (as is shown in FIG. 3). The casing 16 may also include a depression or depressions therein or other ergonomic additions to make the casing 16 easier to grip.

In an exemplary embodiment, the device is 9 cm long from the back of the casing to the tip and the tip is rounded to approximately a 4 mm diameter. However, this is not a limitation on the present invention.

As shown in FIG. 4, in a preferred embodiment, the rod 20 is straight. The ultrasonic energy is transmitted directly to the tip 18 and with the straight rod 20 provides movement in a forward and backward direction (like a piston or jackhammer). The rod 20a bent at a 90 degree angle provides for motion that is parallel to the axis of the rod and causes a back and forth sliding movement at the tip 18.

As shown in FIGS. 6-7, in another exemplary embodiment, the device is approximately 15 cm long from the tip to the base with an extension 19 of about 15 mm in length for connection to a power supply. In another embodiment, the device 10 can include a battery 13 or the like for power supply, which is also shown in FIG. 7. The diameter is approximately 3 cm at the widest and narrowing down to a polished flat tip 18 of approximately 2 mm in diameter. These dimensions are only exemplary and are not a limitation on the present invention.

In use, the ultrasonic energy produced by the transducer 14 is transmitted down the rod 20 and to the tip 18. As shown in FIGS. 6-7, in this embodiment, the rod is cone shaped. However, this is not a limitation on the present invention. Any shape is within the scope of the invention.

In an alternative embodiment, the tip may include a heating element that allows the heat created by the ultrasound energy to be enhanced. As is known in the art, tissue necrosis and pain are initiated at approximately 42.5 degrees centigrade. As is mentioned above, it is desirable to heat the target tissue enough to cause favorable biochemical processes. Accordingly, the heating element can be provided to heat the tissue to a level favorable to provide the biochemical processes described above, but below a level that creates tissue necrosis and pain. In an embodiment of the method, the temperature elevation may exceed 42.5 up to just below 45 degrees with a feeling of warmth and tingling but not pain. In another embodiment, the temperature could be elevated to above 45 degrees. Preferably, the temperature is between about 41 and about 45 degrees centigrade.

With reference to FIGS. 1 and 2 for the anatomy of the eye and FIG. 7, in use, the device 10 is used to apply directed or focused ultrasound to the area overlying the meshwork. In a preferred embodiment, the focal point of the ultrasonic energy is located within about 1 mm of the tip to avoid deeper effects. However, the focal point can be located at a point greater than or less than 1 mm from the tip. For example, the focal point can be 2 mm from the tip. In a preferred embodiment, the focal point is between about 0.001 mm from the tip and about 3.0 mm from the tip. In a more preferred embodiment, the focal point is between about 0.5 mm and about 2.0 mm from the tip. In a most preferred embodiment, the focal point is between about 0.75 mm from the tip and 1.25 mm from the tip. In another embodiment, the ultrasonic energy may be unfocused. For example, focused ultrasound can be applied at 63,500 Hz using 4 watts of power. As can be seen in FIG. 2, the meshwork is located near the area where the cornea and sclera meet. Preferably, anesthetic and/or conduction gel or liquid is placed on the eye (or on the tip 18) and then ultrasonic acoustic energy is applied at the desired frequency, which in turn is transmitted to the trabecular meshwork, thereby dislodging material that is blocking fluid passage and heating the meshwork to initiate heat shock proteins, stimulate matrix metalloproteinase and induce macrophage activity and/or other desired biochemical processes to decrease the pressure.

In operation, the device 10 is moved 360° around the eye over the limbal area, while providing ultrasonic energy to the eye. However, in a preferred embodiment, the tip 18 is not swept around the limbal area of the eye in a 360° path, but instead, the user stops at a number of predetermined points and applies the ultrasonic energy at a predetermined frequency, for a predetermined duration and at a predetermined power. For example, when device 10 is used, the user may stop at twelve equally spaced points similar to the hours on a clock. In another embodiment, with an approximately 4 mm tip, only eight treatment areas may be sufficient. Fewer than eight treatment areas and as few as one treatment area or more than twelve treatment areas can also be used. For example, a patient's anatomy may prevent the placement at twelve treatment areas and may only allow for six treatment areas. When device 40 is used, only four treatments or less may be necessary.

The length of time, the number of treatment areas and the intensity of the ultrasound energy depend on individual cases. In an exemplary embodiment, the procedure may be performed, at about 40,000 Hz with 3 watts of power for about forty five second intervals at about twelve points around the eye. In other procedures, the number of treatment areas may decrease while the treatment time increases when compared to other procedures. Accordingly, none of these numbers are a limitation on the present invention. What is important is that the biochemical changes are triggered by the procedure. Also, in some cases it may be necessary that after such treatment that anterior corneal massage is performed to help flush aqueous humor though the meshwork to help clear the pathway.

In operation, the ultrasonic energy is provided as follows. In a preferred embodiment, the frequency range of the ultrasonic energy is about 10,000 to 500,000 Hz. In a more preferred embodiment, the frequency range is from about 30,000 to 100,000 Hz. In a most preferred embodiment, the frequency range is from about 35,000 to 45,000 Hz. In a preferred embodiment, the duration range is about 5 to about 120 seconds. In a more preferred embodiment, the duration range is about 25 to about 60 seconds and in a most preferred embodiment, the duration range is about 40 to about 50 seconds. In a preferred embodiment, power is provided in the range of about 1 to about 6 watts, with about 3 watts being most preferred. It will be understood that the wattage supplied by the power source may degrade because of the inefficiency of the hand piece. In other words, if the power source supplies about 4 watts of power, the hand piece may only provide about 2 watts of focused ultrasound. As is described above, these ranges will be different for individual cases and therefore, these are not a limitation on the present invention. In an embodiment, the frequency provided, may be outside of the ultrasonic range.

These ranges are low intensity enough to prevent damage to the eye. However, in a preferred, embodiment, the ultrasonic energy applied to the structures of the eye generates heat and sonomechanical acoustic streaming or stable cavitation that is transmitted to the meshwork and helps dislodge the built up material, and initiates biochemical changes to restructure the extracellular matrix and induce macrophage activity as described above.

In a preferred embodiment, to prevent contamination or spread from one patient to another, the exposed tip 18 or 18a of the device 10 can be covered with a small finger cot or condom. With such a cover over the tip there is little or no decrease in the treatment temperature rise than when the treatment is performed without a condom or the like.

In an exemplary embodiment, a device with a round flat tip having a focal point 1 mm from the tip is used. The patient's eye is anesthetized with a topical anesthetic drop, such as tetracaine. The eye is then marked with a marking pen into quadrants near the limbus. Anesthetic ophthalmic gel is used to anesthetize the eye and to provide a contact gel for the ultrasound. The device is tuned to a level of about 3 watts/cm2 at a frequency of between about 39 KHz and about 41 KHz.

The device is placed at a position distal to the cornea allowing approximately 0.5 mm of sclera to be seen between the instrument tip and the cornea. The device is held at angle of approximately 45 degrees from the sclera with the tip aimed at the limbus. Pressure is then exerted on the globe so that the usual limbal curvature is flattened and the globe has a minimal amount of retropulsion. The instrument is applied in this manner for about 45 seconds. During the 45 seconds, it takes about 20 seconds to reach the maximum effect and then 25 more seconds for treatment. The 45 second application is then repeated. The number and positions of these applications is divided equally around the circumference of the eye into 12 clock hours. In controlled studies in which this method was performed, the inventor has found that a reduction of intraocular pressure not only occurs in the treated eye, but also in the contralateral (control) eye. Thus, the method provides a bilateral effect that results in systemic biochemical triggering of the integrins that then lead to the systemic absorption and bilateral cytokine effect.

Thus, by the application of the described focused ultrasound, the method results in the triggering of integrins, and preferably the elevation of the temperature within the treatment area to a level that begins a biochemical cytokine cascade over the meshwork, chamber angle and the ciliary body that is then absorbed systemically leading to a decrease in intraocular pressure in both eyes.

In another embodiment, the device can include a Mems device. In in vitro studies, the temperature of the tissue has been measured using a microthermometer. The inclusion of a Mems device allows for real time measurement of the tissue being treated, which leads to a much more robust instrument where fine tuning the power could allow for much more accurate treatment in an eye that may have a thicker eye wall or in situations where it may be advantages to slightly decrease the potential for inflammation by decreasing the temperature.

The measurement of the amount of pressure exerted against the eye as the tip is applied is a qualitative appreciation of the amount of change in the appearance of the limbal curve as the device is being applied. The result and desired pressure is an appearance of flattening of the limbal arc. A mems device allows the measurement of the pressure and more precise monitoring of the proper application of the pressure.

The angle of the handpiece as the tip is applied to the ocular surface is important because the ultrasound focal point is located 1 mm in front of the tip. The local hyperthermia treatment area has been designed with this configuration to treat the anterior chamber outflow facility without doing damage to the cornea or the ciliary body. An angle of approximately 45 degrees has been found to allow this local area of hyperthermia to match the desired, treatment zone. As the handpiece is moved, around the circumference of the limbus the ability to hold the device at the proper angle can be difficult for the user. However a mems device can provide a more refined or repeatable method by giving feedback or some other method allowing validation of this "angle of attack." For example, the device can include tilt sensors or the like.

In a preferred embodiment, the device includes a box that has a size of about 4" by 8" by 6", which is then attached to the handpiece. The electrical input is currently AC current. However, it can use a rechargeable battery. In another embodiment, the handpiece can omit the software box described above, can have a rechargeable battery that can be placed in a docking station or the like and can be made to be about the size of a marking pen.

FIGS. 8-12 show another preferred embodiment of an ultrasonic device 40 that has a tip member 18 that is shaped to cover more surface area on the eye when compared to the round tip described above and to thereby allow the method to be performed with fewer treatment applications. In this embodiment, the transmission member or rod 20 includes first and second angled extension members 20a and 20b and a tip member 18 that includes a concave portion or concave eye-engaging surface 18a that extends in a width direction and a convex portion 18b that extends in a thickness direction T (see FIG. 11). It will be understood that use of the word "engaging" does not mean that the surface necessarily contacts the eye. As described above in other embodiments, in use, the tip or concave eye-engaging surface can be placed against the eye or held close to the eye, but with a clearance therebetween.

In a preferred embodiment, the arc of the concave eye-engaging surface 18a at the treatment end is about 90°. With a typical corneal diameter being about 11.5 mm, this provides an arc length of about 9 mm and a chord length of about 8.1 mm. These numbers are based on the tip being held against the surface of the eyeball and can change if the operator holds the tip close to but not against the eye. For example, if the tip is positioned about 0.5 mm away from the limbus, the diameter of the circle becomes about 12.5 mm. At this diameter, the arc length is about 9.8 mm and the chord is about 8.8 mm. In a preferred, embodiment, the arc length is between about 6.5 mm and about 11.5 mm. In a more preferred embodiment the are length is between about 7.5 mm and about 10.5 mm. In the most preferred embodiment, the arc length is between 8.0 mm and 10 mm. These numbers are derived from the equation arc length=$2\pi r \times A/360$, where A is 90°. Those of ordinary skill in the art can determine exemplary arc lengths for tip members 18 that include a concave eye-engaging surface 18a with other angles A. For example, if A is 60°, the arc length is preferably between about 5 mm and 7 mm. If A is 120°, the arc length is preferably between about 11 mm and 14 mm. If A is 180°, the arc length is preferably between about 17 mm and 21 mm. However, none of these arc lengths are limitations on the present invention and will depend on the size of the eye. It will be appreciated by those of ordinary skill in the art that the tip may not actually touch the limbus, but instead may rest on the eye away from the limbus and over the sclera.

Figure 12:
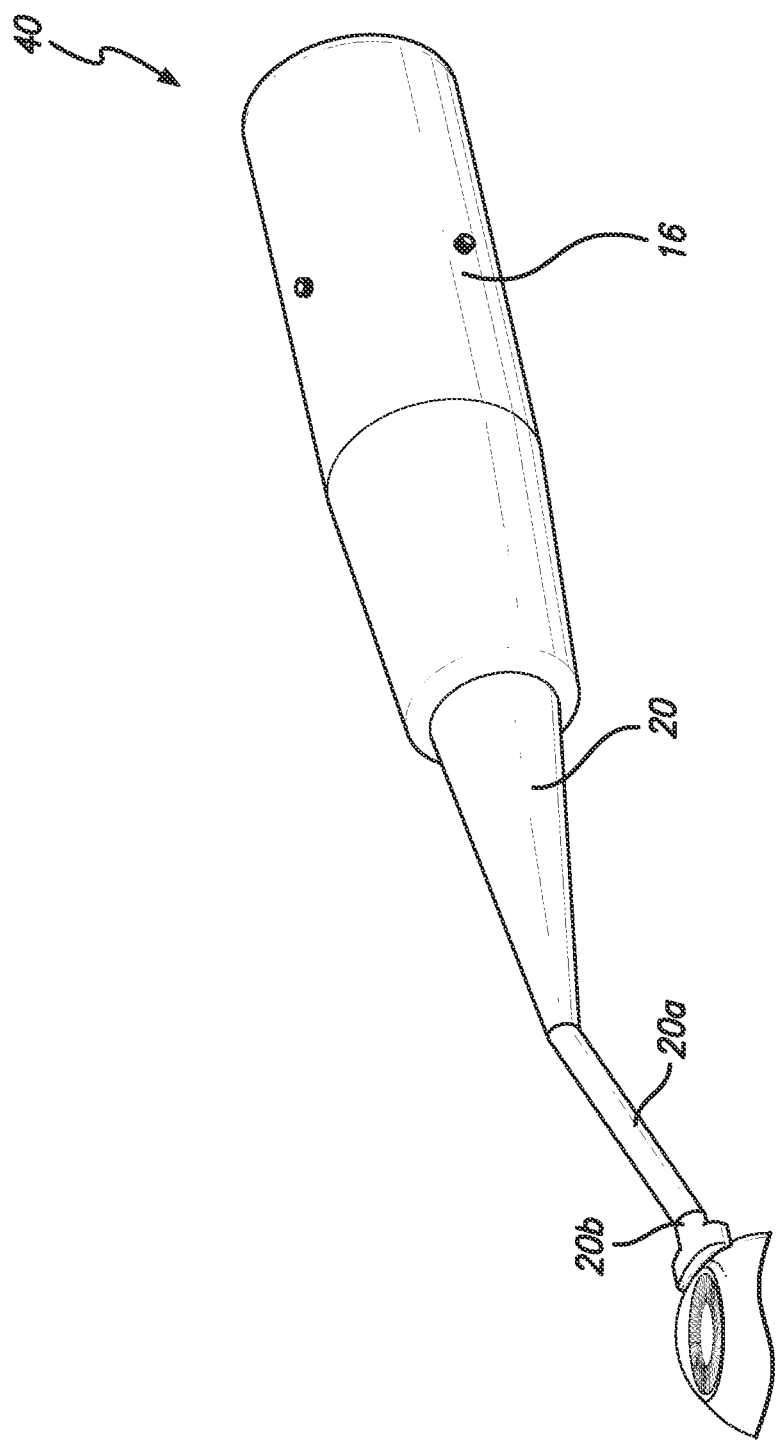
FIG. 12 is a perspective view of the device of FIG. 8 in use.

In a preferred embodiment, the thickness of the tip member 18 is about 2 mm (see arrow T in FIG. 11 showing the thickness direction). However, this is not a limitation on the present invention and the tip member 18 can have a larger or smaller thickness (e.g., between about 0.5 mm to about 10 mm). In use, as shown in FIG. 12, the tip is placed about 0.5 mm away from the cornea on the sclera to avoid any corneal burns. In another embodiment, the tip can be placed at a closer or further distance from the cornea on the sclera. In a preferred embodiment, the tip member 18 includes the convex shape 18b to allow the user to move the tip on the eye (similar to a rocking chair), as desired. These dimensions can be adjusted as desired or based on a larger corneal/limbal diameter.

Figure 8:
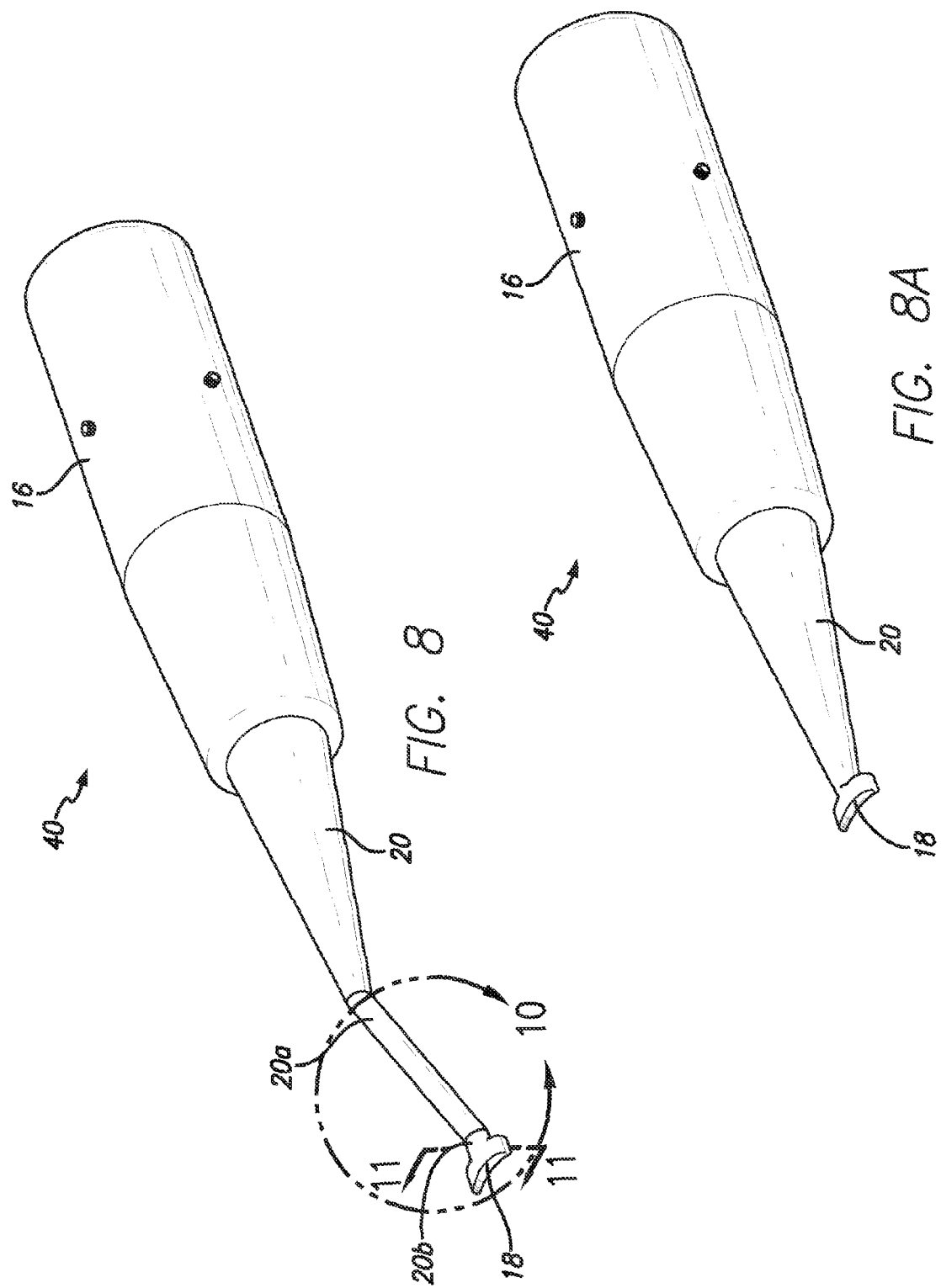
FIG. 8 is a perspective view of an ultrasonic device used for treatment of glaucoma that is used external of the eye in accordance with another preferred embodiment of the present invention.
Figure 9:
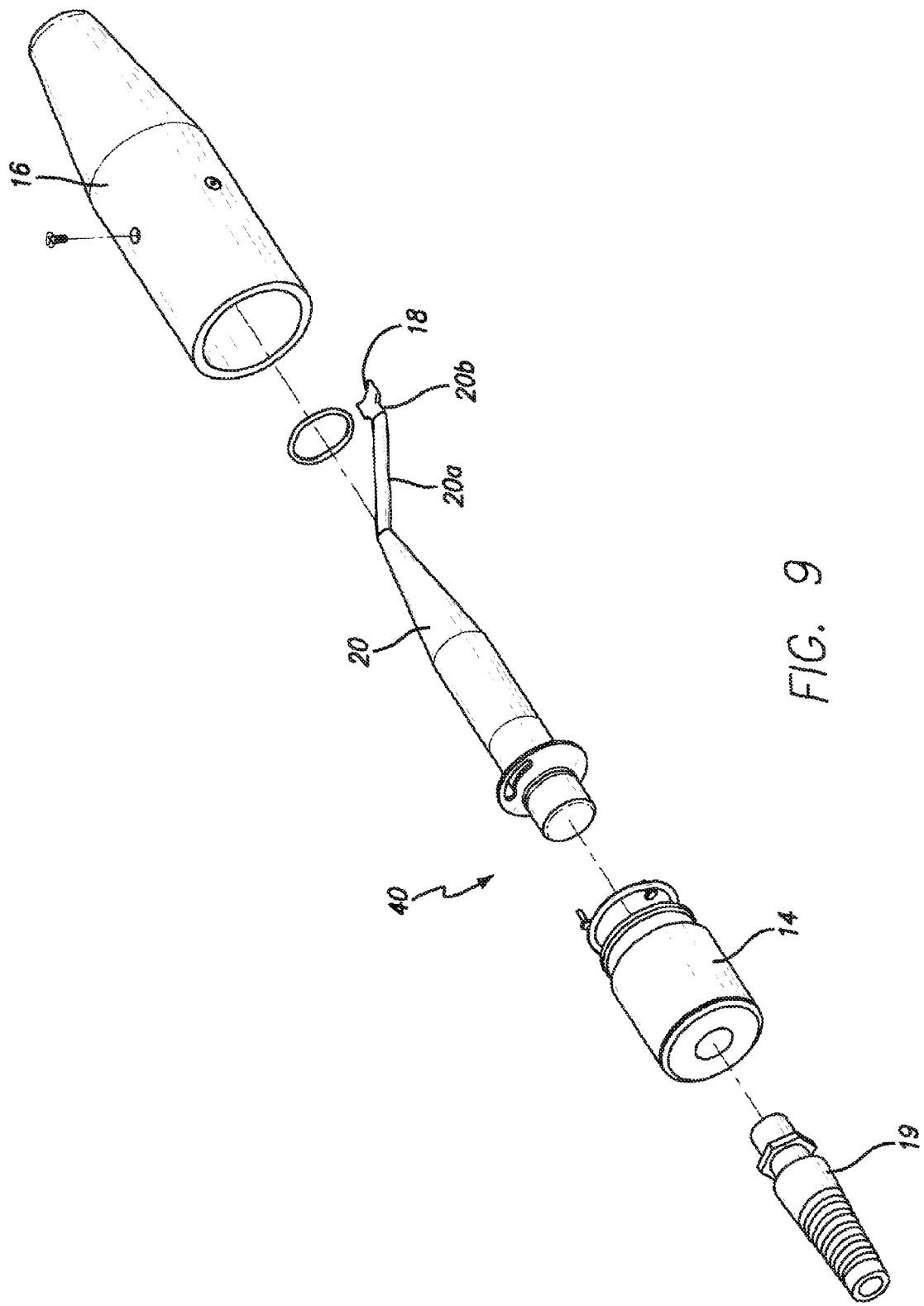
FIG. 9 is an exploded view of the device of FIG. 8.

As shown in FIG. 8, from an ergonomic perspective the rod 20 can have a bend or angle (e.g., 45 degrees) to extension member 20a to allow better visualization by the physician and another bend or angle to extension member 20b to allow application of ultrasonic energy at a comfortable angle as desired. The angled rod 20 allows a better approach to the angle needed at the limbus. Furthermore, the angled rod 20 allows easier access to the portion of the eye that may be blocked by the nose as the treatment progresses around the eye. As shown in FIG. 11, the rod 20 defines a first axis A1 and the first angled extension 20a member defines a second axis A2. In a preferred embodiment, the first axis A1 and second axis A2 are not parallel to one another. The second angled extension member 20b defines a third axis A3. In a preferred embodiment, the first axis A1 and the third axis A3 are about parallel to one another. In this embodiment, the angle θ1 between the rod 20 and the first angled extension member 20a and the angle θ2 between the first angled extension member 20a and the second angled extension member 20b are approximately the same. In another embodiment, the first axis A1 and the third axis A3 are not parallel to one another. θ1 and θ2 can be any angle between 0° and 180°. In another embodiment, rod 20 can be bent or curved and can include extension members that curve or bend and are not necessarily straight as is shown in the figures. In another embodiment, the extension members can be angled to the side and not just downwardly, as is shown.

As shown in FIG. 8A, in another embodiment, the extension members 20a and 20b can be omitted and the curved tip can be located at the end of rod 20 without any bends or angles. In another embodiment, the convex portion 18b can be omitted and the concave portion 18a can include a flat surface.

As shown in FIG. 10A, in a preferred embodiment, either axis A3 (in an embodiment with the first and second angled extension members 20a and 20b) or axis A1 (in an embodiment without the first and second angled extension members 20a and 20b, as shown in FIG. 8A) extends through the center of a circle defined by the arc.

In use, the ultrasonic energy produced by the transducer 14 is transmitted down the rod 20 and to the tip member 18. The 90° arc allows the tip to be placed adjacent the limbus on the sclera such that it covers about 90° or about ¼ of the circle formed by the limbus (i.e., the limbal circumference). In a preferred embodiment, this allows four treatment areas. In other words, with reference to FIG. 12, the first treatment area or first arc is about 0° to about 90° about the limbus, the second treatment area or second arc is about 90° to about 180°, the third treatment area or third arc is about 180° to about 270° and the fourth treatment area or fourth arc is about 270° to about 360°. In another embodiment, the tip can be designed so that it covers up to 45°, 60°, 120°, 180° or 360° to allow 8, 6, 3, 2 or 1 treatment areas. If the tip covers up to 360°, it can be an open circle with an inside diameter of between about 11 mm and about 14 mm with preferably a diameter of about 12.5 mm. The 90 degree arc allows some flexibility over a simple circular tip, for there may be instances where less than 360 degrees is desirable due to potential for inflammation, previous scarring, conjunctival bleb, etc. The parameters discussed above (time duration, power, frequency, etc.) are similar for this embodiment. In another embodiment, the arc can be a number that is not divisible by 360°. For example, the arc can be 100°, thereby allowing some overlap if four treatment areas or arcs are used. In another embodiment, the device can be used without any overlap. For example, the arc can be 80° with four treatment areas or arcs. This provides some play or clearance between treatment areas.

In comparison to the embodiment discussed above, the curved 90° tip can encompass the entire circumference in four treatment areas or applications rather than twelve spots as described above. Furthermore, when treating 12 spots of about 2 mm in size around the eye (wherein the circumference is approximately 36 mm), only about 24 mm of the circumference is actually being treated. With an arc of between 8 and 9 mm, the concave tip can accomplish the 24 mm of actual treatment in 3 applications.

In a preferred embodiment, the entire treatment surface or concave eye-engaging surface 18a transmits ultrasound. In another embodiment, the tip member 18 or the concave eye-engaging surface 18a can include a series of micro arrays within the arc surface or a series of different spots or points that transmit ultrasonic energy. For example, in an embodiment with a 360° tip member, the ultrasonic energy may be transmitted by a number of separate rods or transmission members (e.g., twelve) arranged in a circle to allow twelve treatment areas simultaneously. Similarly, the device may omit the 360° tip member and provide treatment with any number (e.g., twelve) of rods or transmission members that each include a separate tip for treating an arc of the limbal circumference. The tips may be arced, flat, circular or any other shape discussed above.

In use, for sterilization purposes, the user may place a condom over the tip member 18. However, because of the unique shape of the concave tip, the device 40 can be designed to include a disposable or removable tip.

In another embodiment, the device can be miniaturized for ease of use. Any-ultrasonic transducer that allows the method described herein to be performed at the desired parameters is within the scope of the present invention.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description of the Preferred Embodiments using the singular or plural number may also include the plural or singular number respectively. The word "or" in reference to a list of two or more items, covers all of the following interpretations of the word: any of the items in the list, all of the items in the list, and any combination of the items in the list.

The above-detailed description of embodiments of the disclosure is not intended to be exhaustive or to limit the teachings to the precise form disclosed above. While specific embodiments of and examples for the disclosure are described above for illustrative purposes, various equivalent modifications are possible within the scope of the disclosure, as those skilled in the relevant art will recognize. For example, while processes or blocks are presented in a given order, alternative embodiments may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed, at different times. Further any specific numbers noted herein are only examples: alternative implementations may employ differing values or ranges.

The teachings of the disclosure provided herein can be applied to other systems, not necessarily the system described above. The elements and acts of the various embodiments described, above can be combined to provide further embodiments.

Any patents and applications and other references noted above, including any that may be listed in accompanying filing papers, are incorporated herein by reference in their entirety. Aspects of the disclosure can be modified, if necessary, to employ the systems, functions, and concepts of the various references described above to provide yet farther embodiments of the disclosure.

These and other changes can be made to the disclosure in light of the above Detailed Description of the Preferred Embodiments. While the above description describes certain embodiments of the disclosure, and describes the best mode contemplated, no matter how detailed the above appears in text, the teachings can be practiced in many ways. Details of the system may vary considerably in its implementation details, while still being encompassed by the subject matter disclosed herein. As noted above, particular terminology used when describing certain features or aspects of the disclosure should not be taken to imply that the terminology is being redefined herein to be restricted to any-specific characteristics, features or aspects of the disclosure with which that terminology is associated. In general, the terms used in the following claims should not be construed to limit the disclosures to the specific embodiments disclosed in the specification unless the above Detailed Description of the Preferred Embodiments section explicitly defines such terms. Accordingly, the actual scope of the disclosure encompasses not only the disclosed embodiments, but also all equivalent ways of practicing or implementing the disclosure under the claims.

While certain aspects of the disclosure are presented below in certain claim forms, the inventors contemplate the various aspects of the disclosure in any number of claim forms. For example, while only one aspect of the disclosure is recited as a means-plus-function claim under 35 U.S.C. §112, ¶6, other aspects may likewise be embodied as a means-plus-function claim, or in other forms, such as being embodied in a computer-readable medium, (Any claims intended to be treated under 35 U.S.C. §112, ¶6 will begin with the words "means for"). Accordingly, the applicant reserves the right to add additional claims after filing the application to pursue such additional claim forms for other aspects of the disclosure.

Accordingly, although exemplary embodiments of the invention have been shown and described, it is to be understood that all the terms used herein are descriptive rather than limiting, and that many changes, modifications, and substitutions may be made by one having ordinary skill in the art without departing from the spirit and scope of the invention.

What is claimed is:

1. A handheld device for the treatment of glaucoma in an eye that includes a cornea, a sclera and a limbus having a circumference, the device comprising:
    a. a casing,
    b. an ultrasonic transducer,
    c. a power supply,
    d. a transmission member operatively associated with the ultrasonic transducer, and
    e. a tip member located at the end of the transmission member and having a distal end, wherein ultrasonic energy is transferred from the ultrasonic transducer to the tip member, wherein the tip includes a concave eye-engaging surface, wherein the concave eye-engaging surface defines a concave arc and the distal end of the transmission member defines a central longitudinal axis, wherein the central longitudinal axis extends through a center of a circle defined by the concave arc, and wherein the concavity is defined with respect to a point that is distal of the distal end of the tip member and is positioned along the central longitudinal axis.

2. The handheld device of claim 1 wherein the concave arc is between about 45° and about 180°.

3. The handheld device of claim 1 wherein the concave arc is between about 60° and about 120°.

4. The handheld device of claim 1 wherein the concave arc is about 90°.

5. The handheld device of claim 1 wherein the concave arc extends in a first direction, wherein the concave eye-engaging surface includes a convex shape in a second direction that is approximately perpendicular to the first direction.

6. The handheld device of claim 1 wherein the transmission member includes a first angled extension member disposed between the ultrasonic transducer and the tip member, wherein a first portion of the transmission member defines a first axis and the first angled extension member defines a second axis, and wherein the first axis and second axis are not parallel to one another.

7. The handheld device of claim 6 wherein the transmission member includes a second angled extension member disposed between the first angled extension member and the tip member.

8. The handheld device of claim 7 wherein the second angled extension member defines the central longitudinal, and wherein the first axis and the central longitudinal axis are about parallel to one another.

9. The handheld device of claim 4 wherein the concave arc has an arc length of between about 6.5 mm and about 11.5 mm.

10. The handheld device of claim 1 wherein when the concave-eye engaging surface is placed against the sclera, the concave arc extends generally parallel to the circumference of the limbus.

11. The handheld device of claim 1 wherein the concave arc is bifurcated by the central longitudinal axis.

* * * * *